(12) United States Patent
Zinreich et al.

(10) Patent No.: US 8,658,225 B2
(45) Date of Patent: Feb. 25, 2014

(54) HERBAL-BASED NASAL SOLUTION AND METHOD OF USE THEREOF

(75) Inventors: S. James Zinreich, Owings Mills, MD (US); Claus Bachert, St. Martens-Latem (BE)

(73) Assignee: ZNOVA, LLC, Owings Mills, MD (US)

( * ) Notice: Subject to any disclaimer, the term of this patent is extended or adjusted under 35 U.S.C. 154(b) by 160 days.

(21) Appl. No.: 13/141,494

(22) PCT Filed: Dec. 30, 2009

(86) PCT No.: PCT/US2009/069810
§ 371 (c)(1),
(2), (4) Date: Jun. 22, 2011

(87) PCT Pub. No.: WO2010/078419
PCT Pub. Date: Jul. 8, 2010

(65) Prior Publication Data
US 2012/0040030 A1 Feb. 16, 2012

Related U.S. Application Data

(60) Provisional application No. 61/141,729, filed on Dec. 31, 2008.

(51) Int. Cl.
*A61K 36/28* (2006.01)
*A61K 36/539* (2006.01)
*A61K 36/254* (2006.01)

(52) U.S. Cl.
USPC ........... 424/741; 424/764; 424/773; 424/725; 514/474

(58) Field of Classification Search
None
See application file for complete search history.

(56) References Cited

U.S. PATENT DOCUMENTS

| | | | |
|---|---|---|---|
| 6,399,114 B2 * | 6/2002 | Foreman | 424/725 |
| 6,814,985 B1 * | 11/2004 | Hu | 424/725 |
| 2002/0102219 A1 * | 8/2002 | Ross | 424/45 |
| 2003/0012824 A1 | 1/2003 | Ott et al. | |
| 2005/0084454 A1 * | 4/2005 | Fust | 424/45 |
| 2007/0160696 A1 * | 7/2007 | Clymer et al. | 424/756 |
| 2007/0207192 A1 | 9/2007 | Holl et al. | |

FOREIGN PATENT DOCUMENTS

| | | | |
|---|---|---|---|
| JP | 2004238394 A | * | 8/2004 |
| WO | 1996/019228 A1 | | 6/1996 |
| WO | WO 00/41709 A1 | * | 7/2000 |

OTHER PUBLICATIONS

Li, Brown; Efficacy and mechanisms of action of traditional Chinese medicines for treating asthma and allergy; Journal of Allergy and Clinical Immunology; Feb. 2009; pp. 297-306; vol. 123; No. 2.
ISA/KR; PCT/US2009/069810 International Search Report and Written Opinion; Sep. 10, 2010; 9 pages.

* cited by examiner

*Primary Examiner* — Susan Hoffman
(74) *Attorney, Agent, or Firm* — Hahn, Loeser & Parks, LLP

(57) ABSTRACT

A nasal solution and method for treating nasal and sinus inflammation. The nasal solution includes vitamin C, an extract of scutellaria radix, an extract of eleutherococcus radix, an extract of chamomile, and a pharmaceutically acceptable carrier which is suitable for administering the vitamin C, the scutellaria radix extract; the eleutherococcus radix extract; and the chamomile to the nose of a patient. The method includes administering the nasal solution which suppresses early phase and late phase mediators of allergic mucosal disease in order to maintain long-term inhibition of nasal and sinus inflammation.

Figure 1:
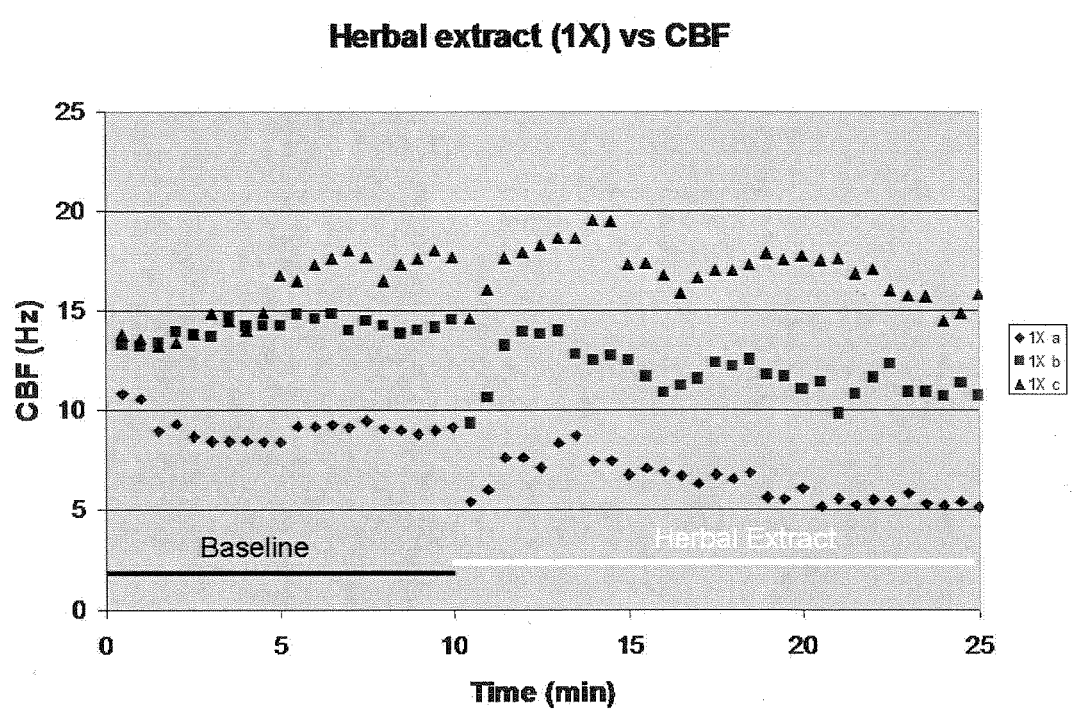

7 Claims, 16 Drawing Sheets

HERBAL-BASED NASAL SOLUTION AND METHOD OF USE THEREOF

CROSS-REFERENCE TO RELATED APPLICATION

This international patent application claims priority to and the benefit of U.S. Provisional Application Ser. No. 61/141,729 filed Dec. 31, 2008, which is incorporated herein by reference.

TECHNICAL FIELD

The invention relates to a solution for local application into the nose and sinuses for treating sinus inflammation. In particular, the invention relates to an herbal-based solution for local application in the nose and sinuses for treating nasal and sinus inflammation. Even more particularly, the invention relates to an herbal-based solution for local application in the nose and sinuses for treating nasal and sinus inflammation which targets and affects T lymphocytes and transforming growth factor beta (TGF-$\beta$).

BACKGROUND OF THE INVENTION

The nose is a complicated structure that serves dual functions as the organ for the sense of smell and as an entry to the respiratory tract. As part of the respiratory tract, a healthy nose moisturizes and warms incoming air and filters out foreign materials.

Nasal passages and other portions of the respiratory tract are lined with specialized tissue layers. In the nose and sinus areas this tissue is often called the nasal mucosa. Like many tissues, the nasal mucosa is composed of several cell layers and cell types. Mucous cells are one type of cell found in the nasal mucosa. Connected to the nose are sinuses or air-filled cavities located behind certain facial bones. There are four groups of sinuses, namely, frontal, sphenoidal, ethmoidal, and maxillary.

Inflammatory disease of the paranasal sinuses is a common disorder afflicting many people. It is characterized by repeated episodes of inflammation, precipitated initially by environmental factors such as smoke, pollutants or allergens, and often followed by a secondary bacterial infection. Exposure to such environmental inhalants stimulates the first stage of an edematous swelling of the membranes of the nose and a partial blockage of sinus drainage. The stroma becomes hyperemic, edematous and infiltrated with neutrophils, lymphocytes, and plasma cells. Serous and mucinous fluid exudes though the epithelium. Clinically these changes manifest as nasal stuffiness and rhinorrhea. If bacterial infection is superimposed, neutrophils dominate the inflammatory infiltrates that become evident as a thick purulent discharge.

The nose and paranasal sinuses represent the predominant contact point between the respiratory system and our environment. As such, it acts as the primary "filter" to cleanse inspired air prior to the process of respiration in the lower airways. Due to this primary function, it is highly susceptible to physiologic and pathophysiologic inflammation. Two common manifestations of this process include allergic rhinitis (affecting 20% of the population with estimated direct costs of $3.4 billion) and chronic rhinosinusitis (affecting 16% of the population with estimated costs of $5.8 billion). Although both disease processes are very different in clinical manifestations they reflect sinonasal inflammation.

The presence of the inflammatory process in the nasal and paranasal mucosa often gives rise to polyp formation. Persistence of these inflammatory changes leads to infiltration by neutrophils, lymphocytes and eosinophils. These inflammatory sequences of events have been well described in the medical literature and many cells have been implicated in this inflammatory process.

Recent research has shown that the type of nasal inflammation may be determined by the role of various T lymphocytes which may co-exist in a nasal tissue (T van Zele et al, Zhang Nan et al). As review, T-cells belong to a group of white blood cells known as lymphocytes, and play a central role in cell-mediated immunity. They can be distinguished from other lymphocyte types, such as B cells and natural killer cells by the presence of specific receptors on their cell surface. It has been shown that in chronic rhinosinusitis with nasal polyps, a deficit in T regulatory cells and the activation of different T effector cells such as Th1, Th2 or Th17 cells exists. These latter cells may orchestrate an inflammatory reaction and also keep T regulatory cells suppressed.

Researchers have begun to consider the effect of cytokine production in nasal inflammation. In particular, interleukins, which are a group of cytokines, are expressed by white blood cells, also known as leukocytes, as a means of communication. Interleukins are produced by a wide variety of body cells. The function of the immune system depends in a large part on interleukins, and rare deficiencies of a number of them have been described, all featuring autoimmune diseases or immune deficiency. Pro-inflammatory and T cell related cytokines are of particular interest.

Researchers have begun to investigate the role of transforming growth factor beta (TGF-$\beta$) in sinus inflammation (N van Bruaene et al). TGF-$\beta$ is known to control proliferation, cellular differentiation, and other functions in most cells. It plays a role in immunity, cancer, heart disease and Marfan syndrome. Some cells secrete TGF-$\beta$, and also have receptors for TGF-$\beta$. This is known as autocrine signaling. Cancerous cells increase their production of TGF-$\beta$, which also acts on surrounding cells. TGF-$\beta$ is a secreted protein that exists in three isoforms called TGF-$\beta$1, TGF-$\beta$2 and TGF-$\beta$3. The TGF-$\beta$ family is part of a superfamily of proteins known as the transforming growth factor beta superfamily, which includes inhibits, activin, anti-müllerian hormone, bone morphogenetic protein, decapentaplegic and Vg-1.

Existing treatments of nasal and sinus inflammation includes the use of antibiotics, both systemic and topical anti-inflammatory agents and decongestants. More recently, topical steroid sprays have been introduced as well as cromolyn which intervenes in this inflammatory process and produces clinical improvement in some of these patients. Unfortunately, many of these patients continue to have advancing disease that leads to total obstruction and a chronic sinusitis. These patients ultimately undergo surgical intervention. The classical surgical techniques involve radical exoneration of polyploid tissue from the nose and paranasal sinuses and the establishment of proper drainage. Such surgery is performed in the hospital under general anesthesia where a fair amount of bleeding is encountered along with some morbidity, not to mention the surgical risks of ocular and intracranial complications of such an extensive sinus surgery.

Other treatments developed over the last two decades have included investigating the mechanism of action of many long time practiced herbal therapies. Many attempts to identify the active components of herbal remedies have concluded that in general no one component is responsible for the therapeutic capacity, but rather the complex and intricate interactions of the herbs result in therapeutic efficacy. Additionally, many of these herbal combinations have demonstrated anti-inflammatory actions. Although the majority of herbal medications are delivered orally, topical applications have also been practiced. Thus, the prospect of managing nasal and paranasal sinus inflammation with topical applications of medicinal herbal extracts is promising.

Recently Jung et al published their findings demonstrating robust reduction of inflammatory parameters, including IL-6, TNF-a, neutrophil density and prostaglandin E2 in the mouse airpouch inflammatory model with root extracts from traditional oriental medicinal plants. Many of these parameters are also found to be increased in Rhinologic diseases. Thus, a topical preparation of herbal extracts and antioxidants were prepared for evaluation. However, prior to confirmation of the anti-inflammatory properties of the extract in a rhinologic model, the preparation should be demonstrated to be safe as a topical application in the nose. Additionally, since bacterial colonization/infection is believed to contribute to the persistent inflammation associated with Rhinosinusitis, antibacterial activity of the preparation should also be undertaken.

Therefore, it would be advantageous to provide an herbal-based solution for a nasal solution that targets and affects specific T effector cells and TGF-$\beta$ present in the nasal tissue in order to maintain long-term inhibition of sinus inflammation.

SUMMARY OF THE INVENTION

In one aspect of the invention is directed to a nasal solution for treating nasal and sinus inflammation. The nasal solution may include vitamin C, scutellaria radix extract, eleutherococcus radix extract, chamomile, a lubricating agent and a pharmaceutically acceptable carrier which is suitable for administering the vitamin C, the scutellaria radix extract; the eleutherococcus radix extract; and the chamomile to the nose of a patient.

In another aspect of the invention is directed to a method of treating nasal and sinus inflammation. The method includes the steps of preparing a nasal solution, wherein the nasal solution comprises vitamin C, scutellaria radix extract, eleutherococcus radix extract, chamomile, a lubricating agent and a pharmaceutically acceptable carrier, and administering the nasal solution to a nasal membrane of a patient diagnosed with nasal inflammation and to sinuses of a patient diagnosed with sinus inflammation.

In yet another aspect of the invention is directed to a method of suppressing early phase and late phase mediators of allergic mucosal disease. The method includes the steps of preparing a nasal solution, wherein the nasal solution includes vitamin C, an extract of scutellaria radix, an extract of eleutherococcus radix, an extract of chamomile, a lubricating agent and a pharmaceutically acceptable carrier, and administering the nasal solution to sinuses of a patient diagnosed with allergic mucosal disease, wherein the nasal solution suppresses the release of prostaglandin D2, an early phase mediator, and the release of late phase mediators including late phase mediators selected from the group consisting of IL-4, IL-5, and IL-13.

BRIEF DESCRIPTION OF THE DRAWINGS

FIG. 1 is a graph representing the lack of toxicity of the herbal-based nasal solution at one-fold concentration on ciliary beat frequency;

FIG. 2 is a graph representing the biofilm preventing efficacy of the herbal-based nasal solution at one-fold concentration against four bacteria;

FIG. 3 shows graphs comparing the effect of the herbal-based nasal solution at 0.5 and 2.5-fold concentrations and fluticasone propionate at different concentrations on the Staphylococcus enterotoxin B-stimulated release of cytokine IL-2;

FIG. 4 shows graphs comparing the effect of the herbal-based nasal solution at 0.5 and 2.5-fold concentrations and fluticasone propionate at different concentrations on the Staphylococcus enterotoxin B-stimulated release of cytokine IFN-γ;

FIG. 5 shows graphs comparing the effect of the herbal-based nasal solution at 0.5 and 2.5-fold concentrations and fluticasone propionate at different concentrations on the Staphylococcus enterotoxin B-stimulated release of cytokine IL-4;

FIG. 6 shows graphs comparing the effect of the herbal-based nasal solution at 0.5 and 2.5-fold concentrations and fluticasone propionate at different concentrations on the Staphylococcus enterotoxin B-stimulated release of cytokine IL-5;

FIG. 7 shows graphs comparing the effect of the herbal-based nasal solution at 0.5 and 2.5-fold concentrations and fluticasone propionate at different concentrations on the Staphylococcus enterotoxin B-stimulated release of cytokine IL-13;

FIG. 8 shows graphs comparing the effect of the herbal-based nasal solution at 0.5 and 2.5-fold concentrations and fluticasone propionate at different concentrations on the Staphylococcus enterotoxin B-stimulated release of cytokine IL-17;

FIG. 9 shows graphs comparing the effect of the herbal-based nasal solution at 0.5 and 2.5-fold concentrations and fluticasone propionate at different concentrations on the Staphylococcus enterotoxin B-stimulated release of cytokine IL-113;

FIG. 10 shows graphs comparing the effect of the herbal-based nasal solution at 0.5 and 2.5-fold concentrations and fluticasone propionate at different concentrations on the Staphylococcus enterotoxin B-stimulated release of cytokine TNF-α;

FIG. 11 shows graphs comparing the effect of the herbal-based nasal solution at 0.5 and 2.5-fold concentrations and fluticasone propionate at different concentrations on the Staphylococcus enterotoxin B-stimulated release of cytokine IL-10;

FIG. 12 shows graphs comparing the effect of the herbal-based nasal solution at 0.5 and 2.5-fold concentrations and fluticasone propionate at different concentrations on the Staphylococcus enterotoxin B-stimulated release of cytokine IL-12 p70;

FIG. 13 shows graphs comparing the effect of the herbal-based nasal solution at 0.5 and 2.5-fold concentrations and fluticasone propionate at different concentrations on the Staphylococcus enterotoxin B-stimulated release of cytokine TGF-β;

FIG. 14 shows a graph comparing the effect of the herbal-based nasal solution at 0.5 and 2.5-fold concentrations on mast cell release of PGD2 upon anti-IgE stimulation;

FIG. 15 shows a graph comparing the effect of the herbal-based nasal solution on nasal inferior turbinate tissue on mast cell release of PGD2 upon anti-IgE stimulation; and FIG. 16 shows a graph comparing the effect of the herbal-based nasal solution on nasal polyp tissue on mast cell release of PGD2 upon anti-IgE stimulation.

DETAILED DESCRIPTION OF THE INVENTION

In general, a nasal solution is provided for local application into the nose and sinuses which targets and affects various T lymphocytes, interleukins and TGF-β in the treatment of nasal and sinus inflammation. The nasal solution generally includes therapeutically effective amounts of vitamin C, scutellaria radix extract, eleutherococcus radix extract, chamomile, and a pharmaceutically acceptable carrier.

In an embodiment of the invention, the nasal solution for treating nasal and sinus inflammation targets different types of T lymphocytes including helper T cells, which are also known as effector T cells or $T_h$ cells.

The $T_h$ cells participate in the adaptive immune system by secreting small proteins called cytokines that regulate or assist in the immune response. Depending on the cytokine signals received, these cells differentiate, for example, into Th1, Th2, Th17 and other cells, which secrete different cytokines. In an embodiment of the invention, it has been determined that various components of the nasal solution target Th1, Th2 and Th17 cells.

In another embodiment of the invention, the nasal solution for treating nasal and sinus inflammation targets and modulates pro-inflammatory cytokines as well as T cell and subset related cytokines. For example, the pro-inflammatory cytokines affected may include IL-1β, tumor necrosis factor-α (TNF-α). Additionally, the T cell and subset related cytokines affected may include interferon-γ, IL-2, IL-4, IL-5, IL-10, IL-12p70, IL-13, IL-17, and TGF-β1.

In one embodiment of the invention, the nasal solution for treating nasal and sinus inflammation may include vitamin C as a component. Vitamin C, also known as L-ascorbate or ascorbic acid, is an effective antioxidant, acting to lessen oxidative stress, a substrate for ascorbate peroxidase, as well as an enzyme cofactor for the biosynthesis of many important biochemicals. Vitamin C also acts as an electron donor for various enzymes. In one embodiment of the invention, vitamin C may provide antioxidant activity to the nasal solution and may inhibit dendritic cell activation. The vitamin C may be present in the nasal solution at a concentration in the range between 0.01 to 0.20% by weight. In one embodiment, the vitamin C may be present in the nasal solution in a concentration at about 0.05% by weight.

In another embodiment of the invention, the nasal solution for treating nasal and sinus inflammation may include an extract of scutellaria radix as a component. Scutellaria radix is the root from Scutellaria baicalensis (or Baikal Skullcap), is a species of flowering plant in the Lamiaceae family. It has been shown to enhance expression of the potentially anti-inflammatory factor TGF-β1 in cultured murine macrophages. It also inhibits neutrophil degranulation. The flavonoid baicalein, which binds to chemokine ligands and inhibits leukotriene C4 synthesis, has been identified as its principal anti-inflammatory active ingredient. In one embodiment of the invention, an ethanol extract of scutellaria radix may provide anti-inflammatory activity for the nasal solution. The scutellaria radix extract may be present in the nasal solution at a concentration in the range between 0.02 to 0.50% by weight. In one embodiment, the scutellaria radix extract may be present in the nasal solution in a concentration at about 0.05% by weight.

In yet another embodiment of the invention, the nasal solution for treating nasal and sinus inflammation may include an extract of eleutherococcus radix as a component. The extract of eleutherococcus radix consists of the dried roots and rhizomes of *Eleutherococcus senticosus*. Although once marketed as "Siberian ginseng", it is not a true ginseng at all. In particular, instead of a fleshy root like most ginseng plants, it has a woody root and instead of ginsenosides, it contains eleutherosides. The extract of eleutherococcus radix is an adaptogen which has a wide range of health benefits attributed to its use. The term adaptogen is used by herbalists to refer to a natural herb product that is proposed to increase the body's resistance to stress, trauma, anxiety and fatigue. It contains eleutherosides, triterpenoid saponins which are lipophilic and which can fit into hormone receptors. The extract of eleutherococcus radix is claimed to possesses a variety of medicinal properties including increased endurance, memory improvement, anti-inflammatory properties, as well as immunogenic, chemoprotective and radiological protection. In one embodiment of the invention, an ethanol extract of eleutherococcus radix may provide anti-inflammatory activity for the nasal solution. The eleutherococcus radix extract may be present in the nasal solution at a concentration in the range between 0.02 to 0.50% by weight. In one embodiment, the scutellaria radix extract may be present in the nasal solution in a concentration at about 0.05% by weight.

In yet another embodiment of the invention, the nasal solution for treating nasal and sinus inflammation may include an extract of chamomile as a component. Chamomile may refer to any of several distinct species in the sunflower family Asteraceae. Chamomile is a commonly used anti-inflammatory medicinal herb used in Europe, but it is also popular in Central and South America. Chamomile extracts have been shown to be effective in the topical treatment of chronic skin inflammation such as atopic dermatitis, and also recurrent oral aphthous ulcers. Chamomile contains several anti-inflammatory compounds, notably etheric oils and flavonoids. Chamomile-based products for topical applications, including nasal and oral sprays, are commercially available as Kamillosan®. In one embodiment of the invention, an ethanol extract of chamomile may provide anti-inflammatory activity for the nasal solution. The chamomile extract may be present in the nasal solution at a concentration in the range between 0.1 to 1.0% by weight. In one embodiment, the scutellaria radix extract may be present in the nasal solution in a concentration at about 0.1% by weight.

In another embodiment of the invention, the nasal solution for treating nasal and sinus inflammation may also include a lubricating agent. For example, the lubricating agent may be glycerol. Glycerol is a colorless, odorless, viscous liquid that is widely used in pharmaceutical formulations. Glycerol is a sugar alcohol and has a low toxicity. The glycerol in the nasal solution may act not only as a lubricating agent, but also as a humectant, which is a hygroscopic substance that provides moisturization. Therefore, the glycerol component of the nasal solution may lubricate, as well as moisturize, the nasal passages after local application within the nose and sinuses. The lubricating agent may be present in the nasal solution at a concentration in the range between 0.01 to 0.15% by weight. In one embodiment, the lubricating agent may be present in the nasal solution in a concentration at about 0.01% by weight.

In another embodiment of the invention, the nasal solution for treating nasal and sinus inflammation may include a pharmaceutically acceptable carrier as a component. By "pharmaceutically acceptable carrier", it is meant to be a composition, solvent, dispersion medium, coating, delivery vehicle or the like, which can be employed to administer the compositions of the present invention without undue adverse physiological effects. Suitable pharmaceutically acceptable carriers used in preparing the nasal solution of the invention preferably include diluents such as normal saline, isotonic saline solution, including 0.9% saline solution, deionized water and Ringer's lactate solution. In one embodiment of the invention, the pharmaceutically acceptable carrier is Ringer's lactate solution that is a solution of sodium, chloride, potassium and lactate which come from NaCl (sodium chloride), NaC$_3$H$_5$O$_3$ (sodium lactate), CaCl$_2$ (calcium chloride), and KCl (potassium chloride). The pharmaceutically acceptable carrier may be present in the nasal solution at a concentration in the range between 98.70 to 99.90% by weight. In one embodiment, the pharmaceutically acceptable carrier may be present in the nasal solution in a concentration at about 99.74% by weight.

The nasal solution may also include pharmaceutically acceptable additives. The additives, as used herein, include excipients or stabilizers which are nontoxic to the patient being exposed thereto at the dosages and concentrations employed. Often the pharmaceutically acceptable additive is an aqueous pH buffered solution. Examples of physiologically acceptable carriers include buffers such as, but not limited to, phosphate, borate, citrate and other organic acids; carbohydrates including glucose, mannose, or dextrins; chelating agents such as EDTA; and sugar alcohols such as mannitol or sorbitol.

A preservative may also be optionally used to maintain the integrity of the nasal solution. Suitable preservatives are well known to those skilled in the art and include sorbates, benzoates and mixtures thereof. However, a small quantity (e.g., less than 1% by volume) of potassium sorbate, potassium benzoate or mixtures thereof may be added to the composition.

The following Examples illustrates the components, as well as amounts, of the nasal solution for treating nasal inflammation, but these examples are not considered to be limiting the scope of this invention.

EXAMPLE 1

A nasal solution of the following composition may be used for treating nasal and sinus inflammation may include a range of components including:

| Nasal Solution | | |
| --- | --- | --- |
| Component | Lower Range(g) | Upper Range(g) |
| *Scutellaria* radix extract | 0.2 | 5.0 |
| *Eleutherococcus* radix extract | 0.2 | 5.0 |
| Chamomile extract | 1.0 | 10.0 |
| Vitamin C | 0.1 | 1.0 |
| Glycerol 85% | 0.1 | 1.0 |
| 0.9% Isotonic saline solution | 987.0 | 998.4 |
| Total | 1000.0 | 1000.0 |

EXAMPLE 2

A first nasal solution based upon the range of Example 1 of the following composition may be used for treating nasal and sinus inflammation:

| Nasal Solution | | |
| --- | --- | --- |
| Component | Amount (g) | Weight % |
| *Scutellaria* radix extract | 0.5 | 0.05 |
| *Eleutherococcus* radix extract | 0.5 | 0.05 |
| Chamomile extract | 1.0 | 0.10 |
| Vitamin C | 0.5 | 0.05 |
| Glycerol 85% | 0.1 | 0.01 |
| 0.9% Isotonic saline solution | 997.4 | 99.74 |
| Total | 1000.0 | 100.00% |

EXAMPLE 3

A second nasal solution, which is outside the range as detailed in Example 1, of the following composition may be used for treating nasal and sinus inflammation:

| Nasal Solution | | |
| --- | --- | --- |
| Component | Amount (g) | Weight % |
| *Scutellaria* radix extract | 1.22 | 0.18 |
| *Eleutherococcus* radix extract | 2.24 | 0.33 |
| Chamomile extract | 1.76 | 0.26 |
| Vitamin C | 0.70 | 0.10 |
| Glycerol 85% | 0.81 g | 0.12 |
| Ringer-Lactate Solution | 673.27 | 99.01 |
| Total | 680.00 | 100.00% |

EXAMPLE 4

A third nasal solution, which is outside the range as detailed in Example 1, of the following composition may be used for treating nasal and sinus inflammation:

| Nasal Solution | | |
| --- | --- | --- |
| Component | Amount (g) | Weight % |
| *Scutellaria* radix extract | 1.22 | 0.18 |
| *Eleutherococcus* radix extract | 2.24 | 0.33 |
| Chamomile extract | 1.76 | 0.26 |
| Vitamin C | 0.70 | 0.10 |
| Glycerol 85% | 0.81 g | 0.12 |
| 0.9% Isotonic saline solution | 673.27 | 99.01 |
| Total | 1000.0 | 100.00% |

Tests were conducted to investigate the toxicity effect of the nasal solution. First, nasal septa of mice were harvested as previously described (Antunes, B. A. et al. 2007). Briefly, following euthanasia, the skin is reflected to expose the bone over the entire skull and nose. The skull is sectioned in the coronal plane posterior to the eyes. A scissor is inserted into the posterior aspect of the nasal cavity and the suture line that represents the embryonic fusion plane formed between the maxilla and ethmoid bone is cleaved. The palate is then sectioned to separate the septum from the lateral nasal wall. The procedure is then repeated on the other side and the septum completely removed.

Next, harvested murine nasal septa are placed in Locke Ringer's solution [136 mM NaCl, 5.6 mM KCl, 10 mM HEPES, 14.3 mM NaHCO$_3$, 1.2 mM MgCl$_2$, 2.2 mM CaCl$_2$ and 11.5 mM dextrose, pH 7.35] in a pre-filled observation chamber (Warner Inst., Hamden Conn.) and held in place with a nylon grid (1.5 mm). The stage and solution of the observation chamber are maintained at a temperature between about 35.5° C. and about 37° C. with a dual channel heater (Warner Inst., Hamden Conn.). Additional solution, at temperature, can be added to maintain submersion of the tissue. Images are visualized using a Leica DMLFSA microscope using a water immersion 63× objective and differential interference contrast (DIC) optics (Leica Microsystems, Inc., Bannockburn, Ill.). Images are captured using a Model A602f-2 Basler area scan high-speed monochromatic digital video camera (Basler A G, Ahrensburg, Germany) at a sampling rate of 100 frames per second with a resolution of 640×480 pixels. The video images were analyzed using the Sisson-Ammons Video Analysis (SAVA) system version 2.1 (Sisson, Stoner et al. 2003). For each experiment, beating cilia on the edge of the explant was detected with the upright microscope. The digital image signal was then routed from the camera directly into a digital image acquisition board (National Instruments) within a Dell XPS 710 Workstation running Windows XP Professional operating system. Images were captured, compressed, and stored to disk. Files were then reloaded and analyzed with virtual instrumentation software highly customized to perform cilia beat frequency (CBF) analysis. Recordings proceeded every 30 seconds until a stable baseline was obtained (usually 5-10 minutes). The test solutions were than perfused onto the explant to flood the perfusion chamber and clamped (as to not induce mechanical stimulation). CBF was recorded about every 30 seconds for about 15 minutes and assessed for disruption of cilia activity. Two concentrations of test solution were assessed in at least duplicate.

Although the respiratory epithelium is comprised of many cell types, the predominant cell is the pseudo-stratified columnar ciliated cell responsible for generating the propulsive force transporting debris laden mucus to the glottis for elimination. Therefore, maintaining and preserving the ciliary function is a consideration for any therapeutic intervention that is involved with the nose and paranasal sinuses. Utilizing a Sissons Ammons Video Analysis (SAVA) system, the acute effects of the herbal preparation were evaluated at an approximately five-fold concentration on freshly harvested mouse nasal septa. As seen in FIG. 1, baseline cilia beat frequency (CBF) was obtained for about 10 minutes (black line) prior to application of the herbal extract (white line). Cilia beat frequency was continuously monitored for an about additional 15 minutes following application of test substance. As demonstrated in FIG. 1, application of the five-fold concentration of the herbal extract negatively affected the ciliary beat frequency.

Tests were also conducted to investigate the antibacterial efficacy of the nasal solution. Bacterial and biofilm growth inhibition was determined using the plate based assay described in Moskowitz et al. (Moskowitz, Foster et al. 2004). Briefly, PAOI *Pseudomonas aeruginosa* bacterial strain and clinical isolates (1535, 1685, and 1798) were grown overnight. The next morning, the culture was diluted to an $OD_{600}=0.1$ with LB and the sample again diluted 1:100 in LB. About 100 µl of diluted bacteria was added to about 25 µl of a 5× concentrations of test solutions diluted in LB), placed in 96 well flat bottom plates (catalog number 269787, Nalgene Nunc International, Rochester N.Y.) in quadruplicate. A modified polystyrene microtiter lid with 96 pegs (catalog number 445497; Nunc TSP system) was placed into the bacterial isolate growth plate. The covered 96 well plates were incubated for about 20 hours at about 37° C. At the completion of the incubation the lid containing the pegs was removed and processed for biofilm detection while the 96 well plates were analyzed for bacterial growth by determination of absorbance at 600 nm. After incubation, the peg lid was rinsed three times in sterile water and the lid was placed in 2% crystal violet solution (Remel Inc, Lenexa Kans.) for about 30 minutes to stain the biofilms adherent to the pegs. The peg lid was then rinsed again three times in sterile water, and dried for about one hour. Next, the peg lid was inserted into a 96-well microtiter plate containing a 100% ethanol solution for about 15 minutes. The peg lid was then discarded and the eluted crystal violate was read on a microtiter plate reader (Microplate Reader 680, Bio-Rad Hercules, Calif.) at an optical density of 595 nm ($OD_{595}$).

Figure 2:
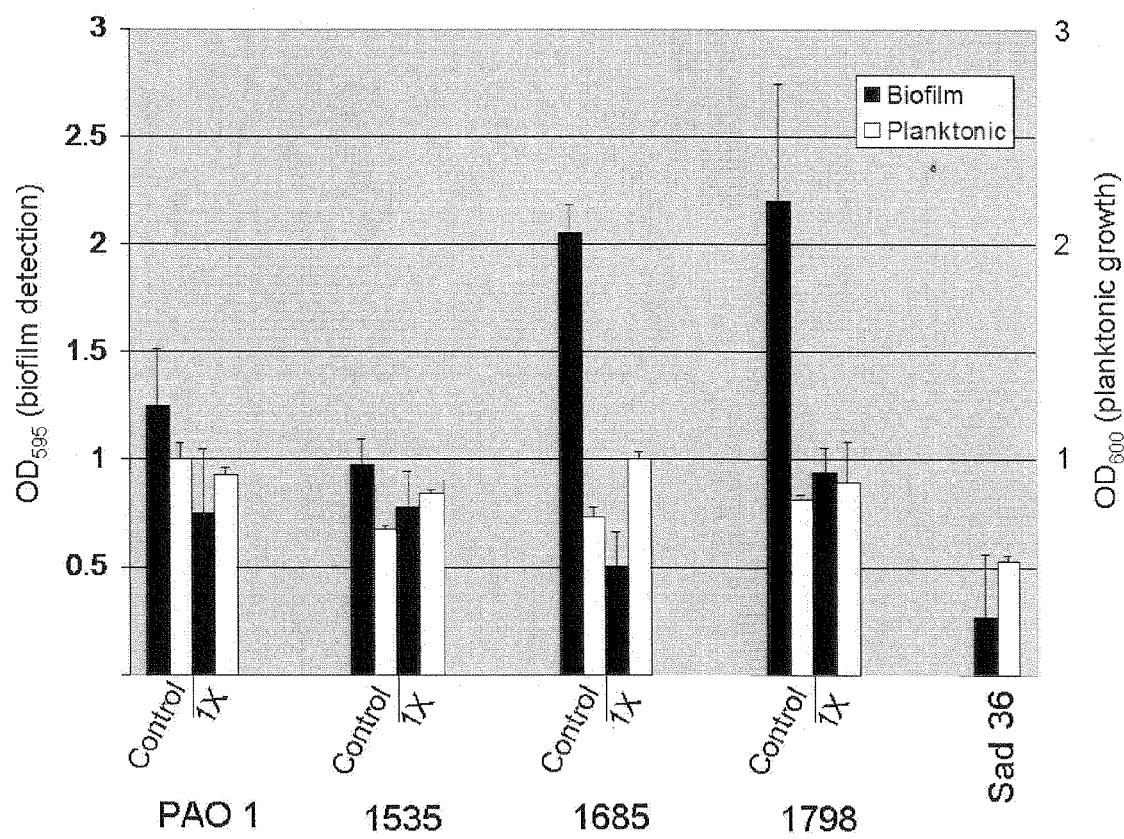

The antibacterial capacity of the herbal-based nasal solution was determined through a modification of the Calgary Biofilm Detection assay that was employed to assess inhibition of planktonic growth as well as well as biofilm formation. The assay was run against 4 bacteria, commercially available PAOI (*Pseudomonas aeruginosa*) as well as 3 bacteria isolated from patients with medically recalcitrant Chronic Rhinosinusitis (1535, 1685 and 1798 all *Pseudomonas aeruginosa*). As seen in FIG. 2, inhibition of biofilm formation (blue bars) is demonstrated with the herbal-based nasal solution in 3 of the four bacteria tested.

In summary, as a topical sinonasal preparation, the anti-inflammatory herbal-based nasal solution may be considered safe, as it causes substantially no ciliotoxicity. The herbal-based nasal solution also appears to have some antibiofilm formation properties. This component may have therapeutic relevance to patients with medically recalcitrant chronic rhinosinusitis (CRS) as it is recently been demonstrated that the presence of biofilms correlates to poor clinical evolution in CRS.

Further studies were performed to investigate the modulation of cytokine production after stimulation with Staphylococcus aureus derived protein enterotoxin B (SEB) by the herbal-based nasal solution in human nasal polyp tissue. A pH-assessment and a PBL-toxicity-assay were performed before the assays. Tissue fragments were stimulated with RPMI (negative control) and enterotoxin B for about 24 hours. Supernatants were measured by Multiplex for pro-inflammatory cytokines (IL-1β, tumor necrosis factor-α) and T cell and subset related cytokines (interferon-γ, IL-2, IL-4, IL-5, IL-10, IL-12p70, IL-13, IL-17, and TGF-β1).

Nasal tissue was obtained from 5 patients at the Department of Otorhinolaryngology of the University Hospital of Ghent. The ethical committee of the Ghent University Hospital approved the study and all patients gave their written informed consent prior to inclusion in the study. None of the subjects received intranasal corticosteroids, anti-histamines or anti-leukotrienes, oral and intranasal decongestants or intranasal anticholinergics within 1 week prior to surgery and none of the subjects received oral and/or intramuscular corticosteroids within 4 weeks prior to surgery. For female subjects pregnancy or lactation was excluded.

Nasal polyp samples were collected during functional endoscopic sinus surgery from 5 subjects with nasal polyps. Nasal polyposis was diagnosed based on symptoms, clinical examination, nasal endoscopy, and sinus computed tomography (CT) scan according to the $EP^3OS$ guidelines. The nasal tissue collected during surgery was immediately transported to the laboratory and used for the ex-vivo stimulations.

The human nasal mucosa and submucosa was cut thoroughly in tissue culture medium (TCM) consisting of RPMI 1640 (Sigma-Aldrich, Bornem, Belgium), containing 2 mM L-Glutamine (Invitrogen, Merelbeke, Belgium), antibiotics (about 50 IU/ml penicillin and about 50 µg/ml streptomycin) (Invitrogen) and about 0.1% BSA (Bovine Serum Albumin, Sigma). The tissue was passed through a mesh to achieve comparable fragments. The tissue fragments (+/−0.9 $mm^3$) were weighed and resuspended as about 0.04 g tissue/1 ml tissue culture medium.

The tissue fragments were stimulated with culture medium (negative control) and about 0.5 μg/ml SEB from Sigma-Aldrich for about 24 hours. After that, tissue fragments and supernatants were separated by centrifugation. Aliquots of the supernatants were taken and stored immediately at about −20° C. until analysis of cytokines by Luminex according to the manufacturer's guidance.

Regarding the results, the pH-assessments showed normal, physiological values for all dilutions used. No toxicity was observed for the lower concentrations of the solutions, whereas the tenfold solution diluted about 1:2 showed about a 39% reduction of viable cells.

In general, SEB stimulation over a period of about 24 hours induced an increase of interferon-γ (IFN-γ), IL-2, IL-4, IL-5, IL-13 and IL-17. The solution reduced the SEB-stimulated release of cytokines IL-2, IFN-γ and IL-17 dose-dependently, and the spontaneous and stimulated release of IL-4, IL-5, IL-13, IL-17, IL-1β, TNF-α, and TGF-β1 dose-dependently. The effects were in all cases equivalent to or superior to commercially available fluticasone propionate, a well established topical corticosteroid for nasal use.

A discussion of the test results for the modulation of cytokine production after stimulation with SEB by the herbal-based nasal solution follows. The following abbreviations are utilized while discussing the results:

| Solution | Abbreviation |
|---|---|
| Herbal-based nasal solution at a 0.5-fold concentration | C1 |
| Herbal-based nasal solution at a 2.5-fold concentration | C2 |
| Fluticasone propionate in concentrations from $10^{-10}$ to $10^{-8}$ | FP |
| Tissue culture medium (control) | TCM |

Figure 3:
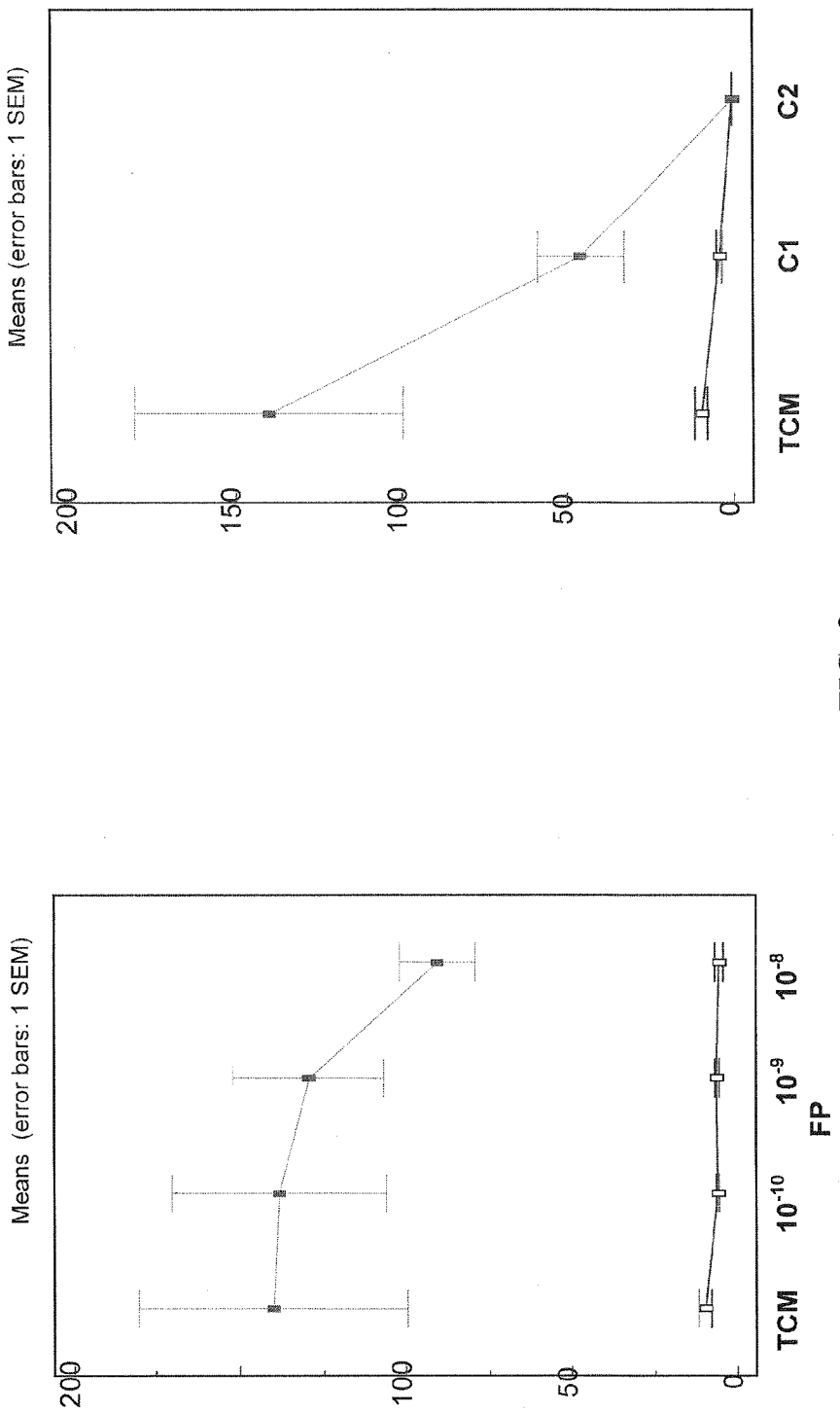
Figure 4:
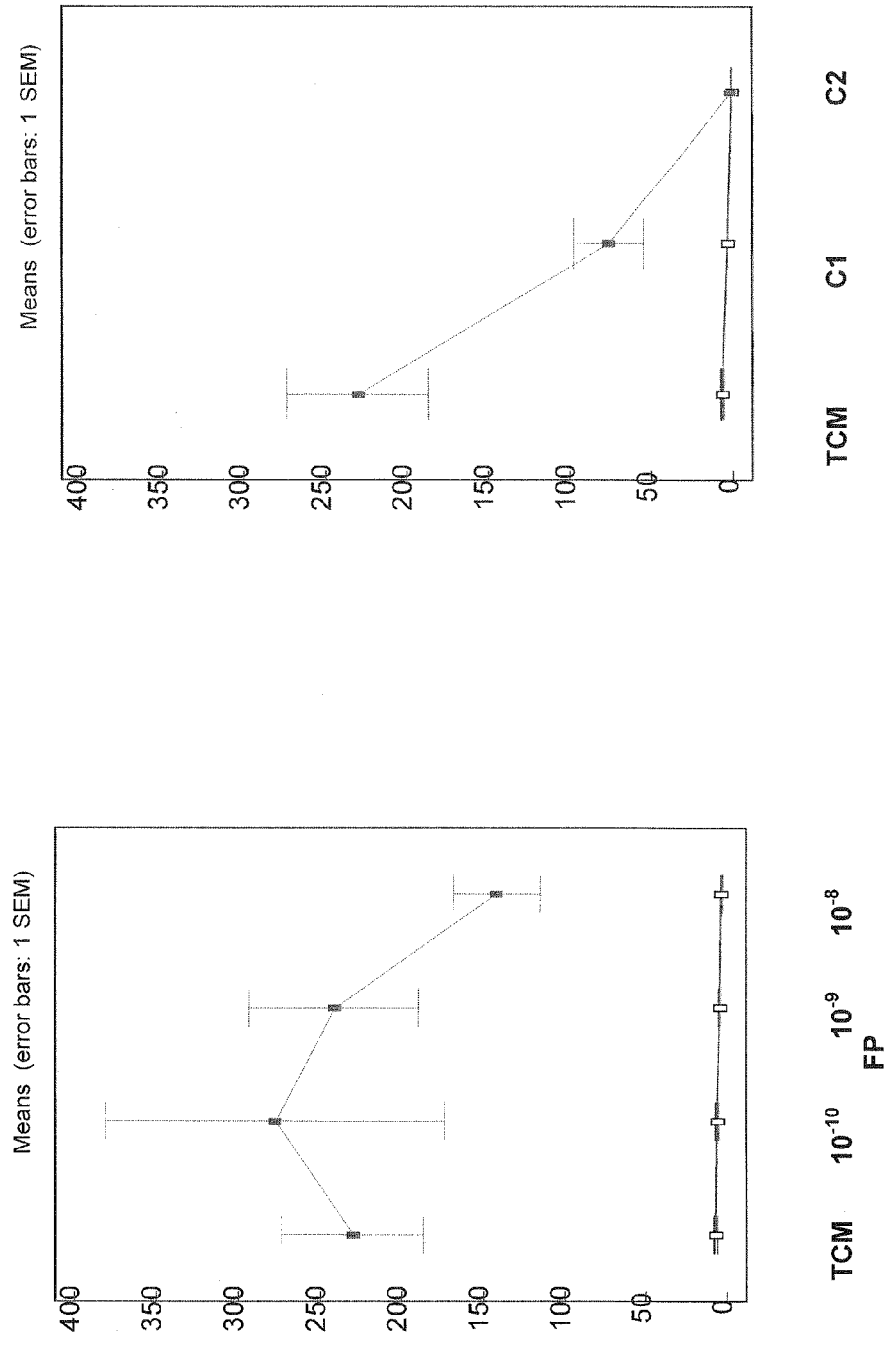
Figure 5:
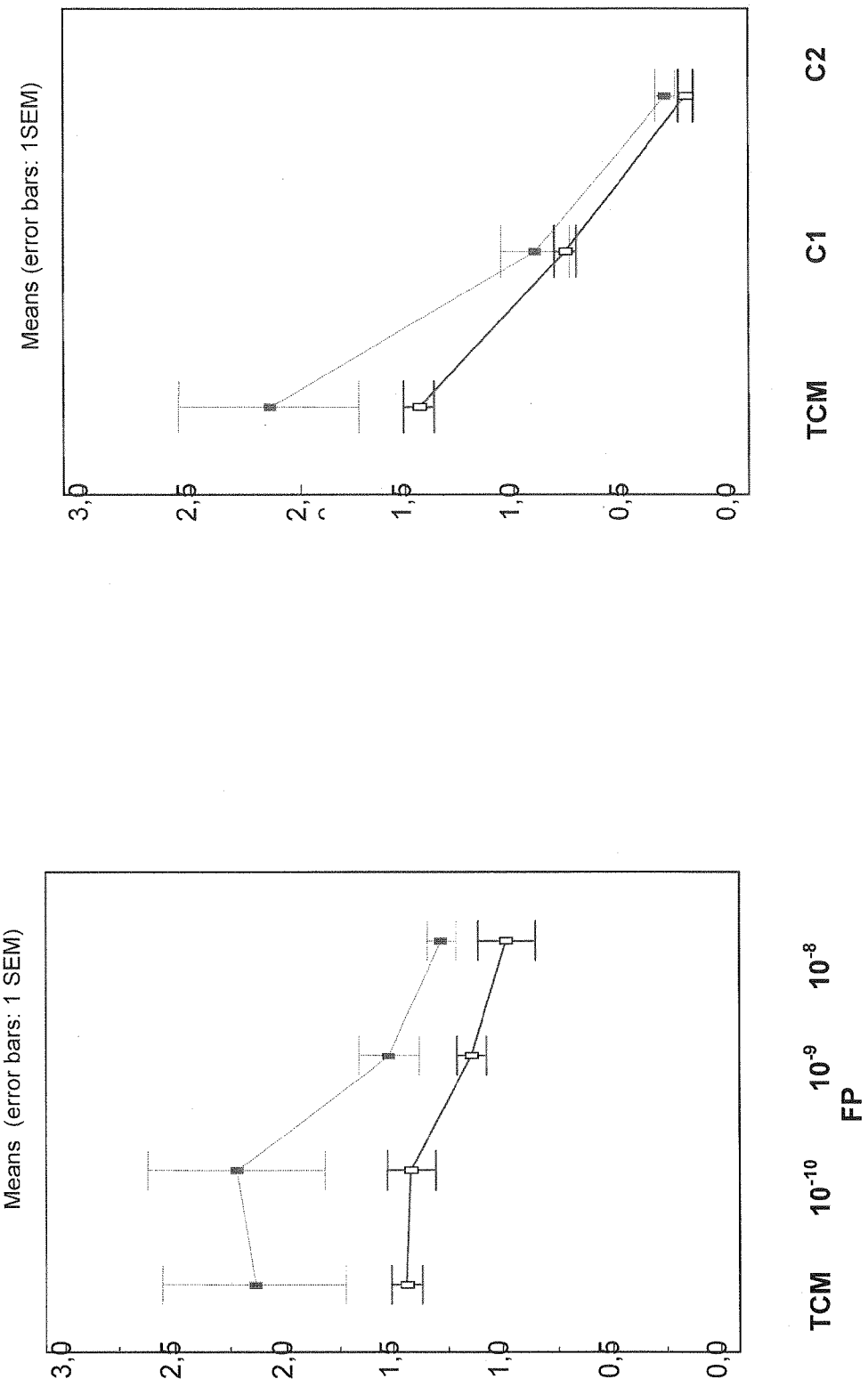
Figure 6:
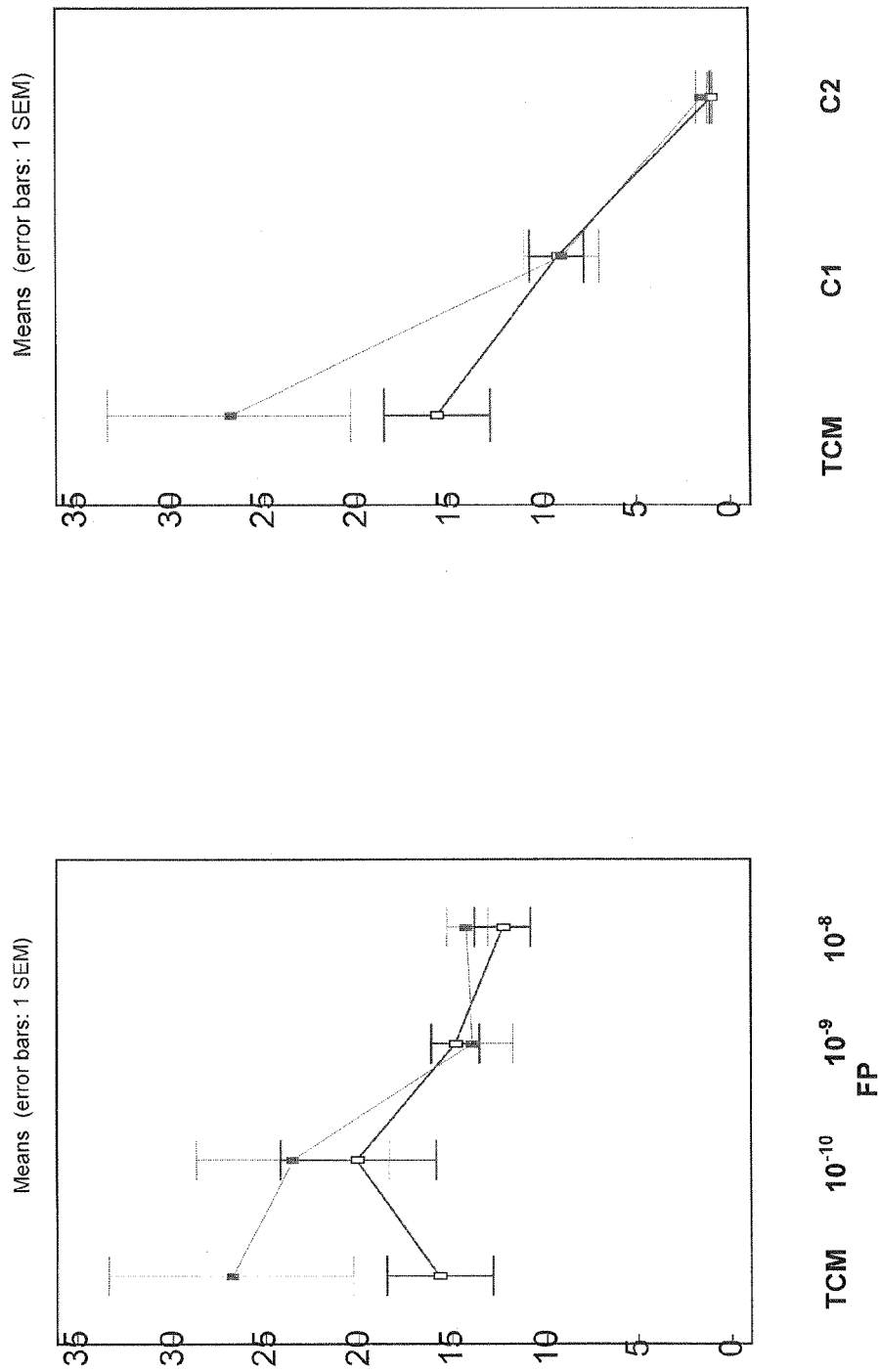
Figure 7:
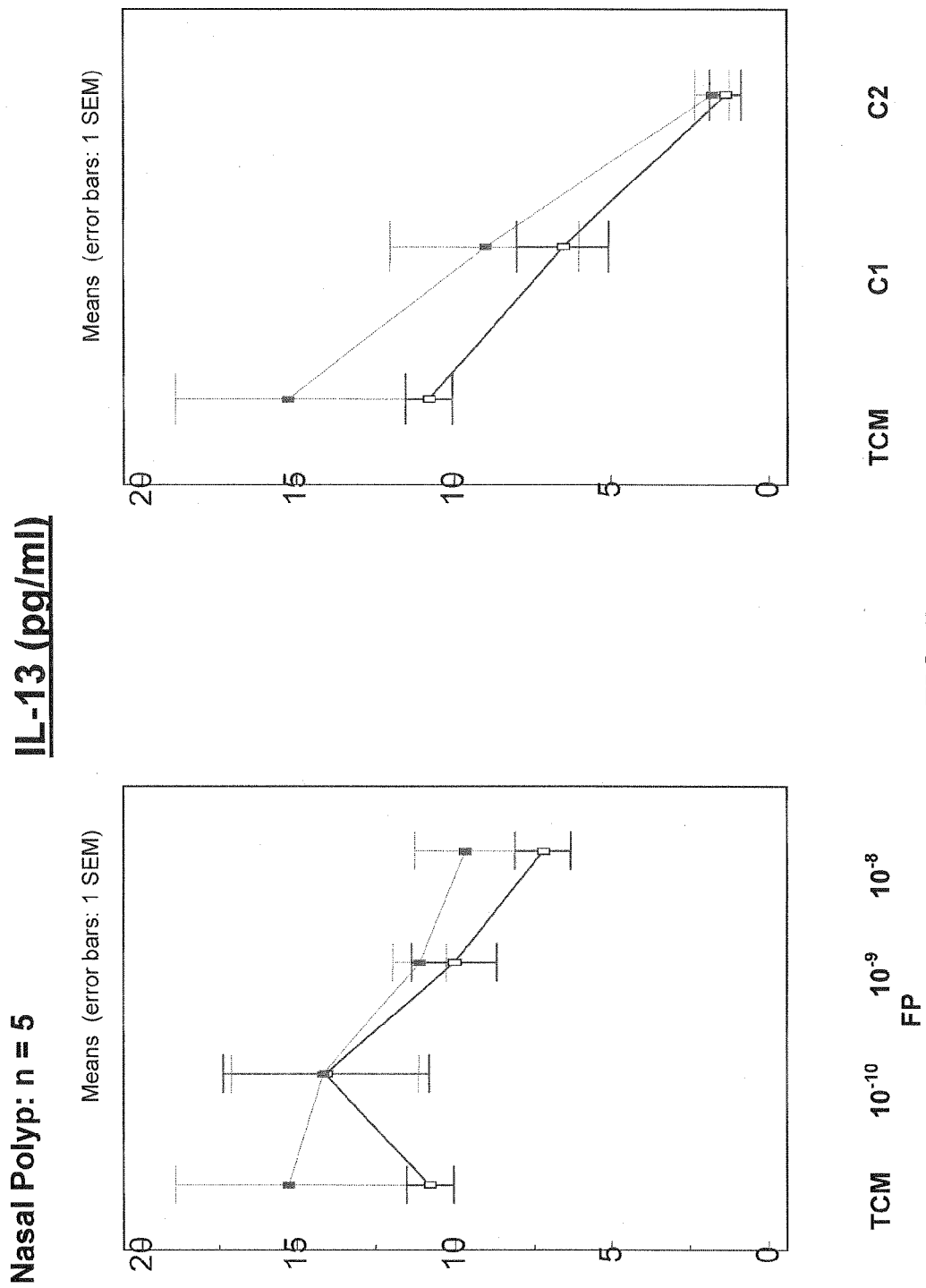
Figure 8:
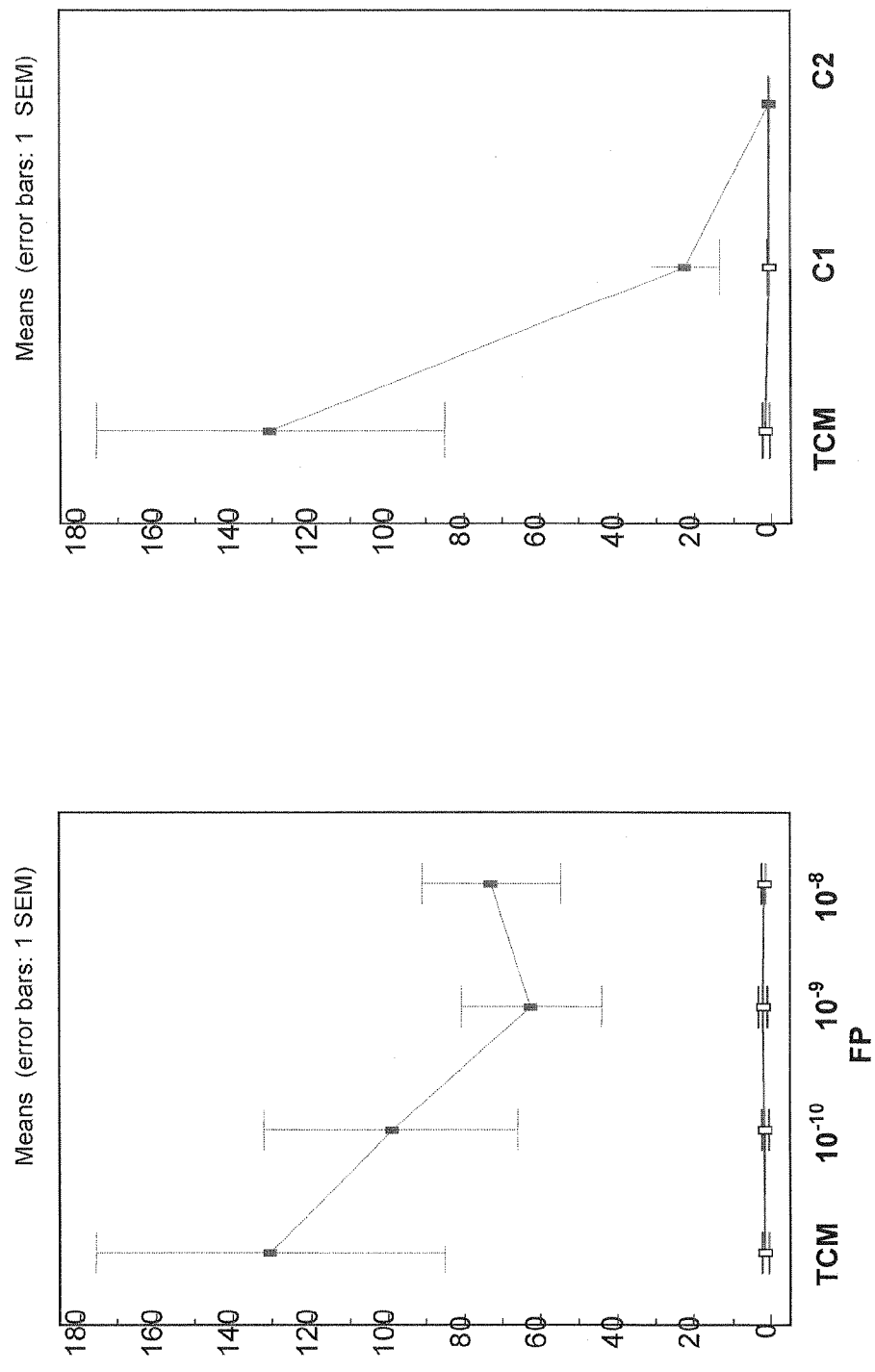
Figure 9:
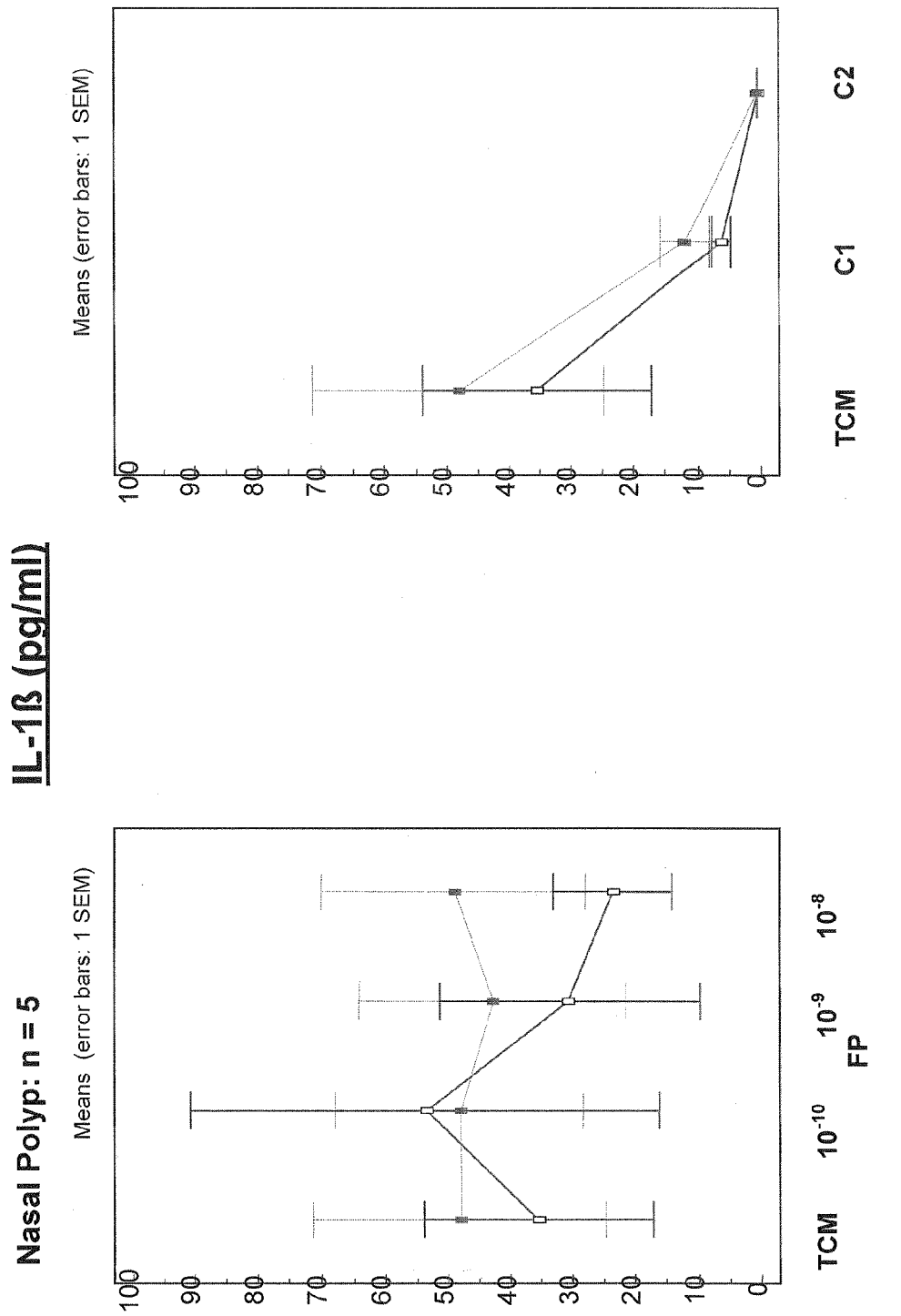
Figure 10:
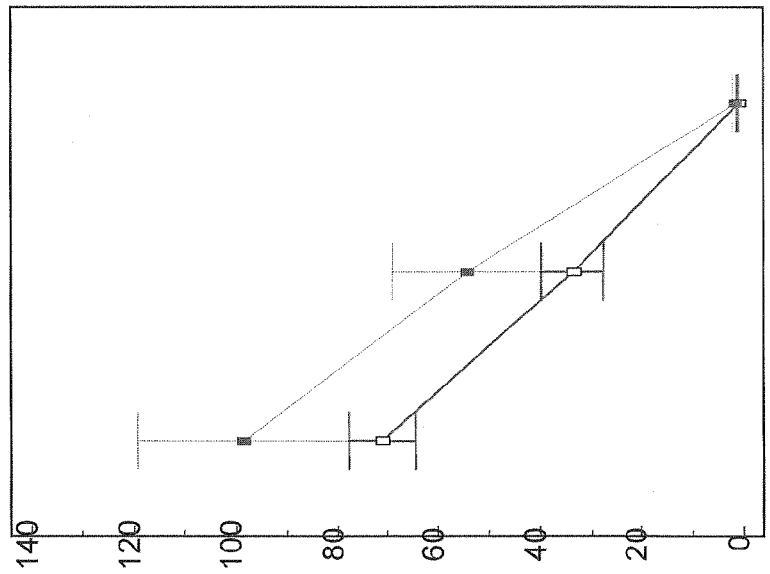
Figure 10:
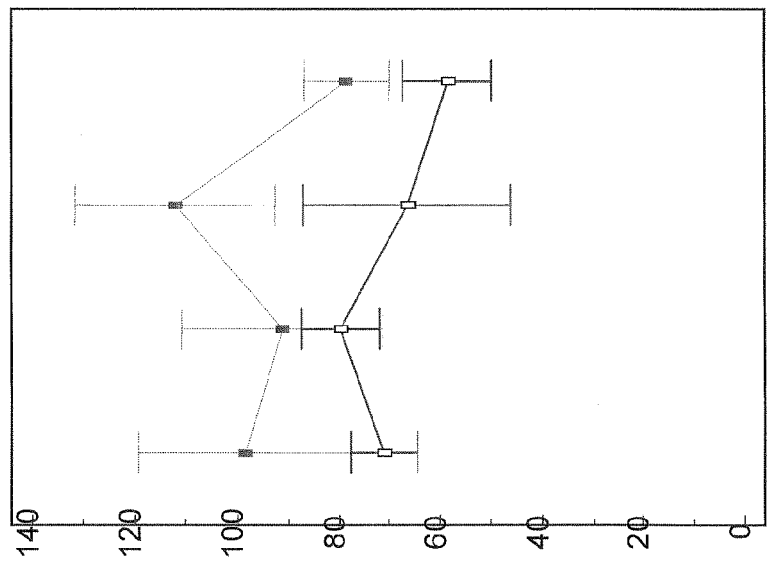
Figure 11:
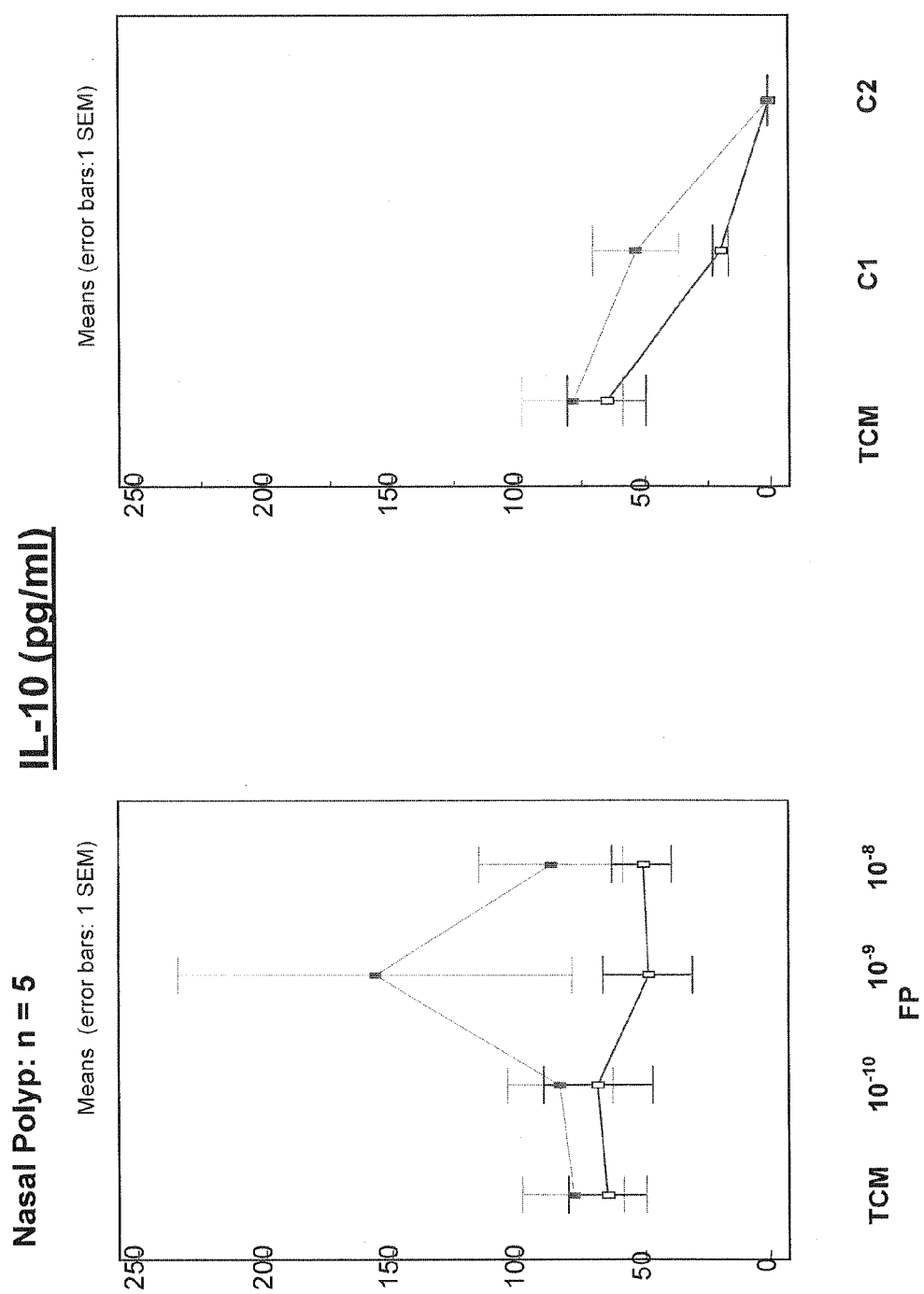
Figure 12:
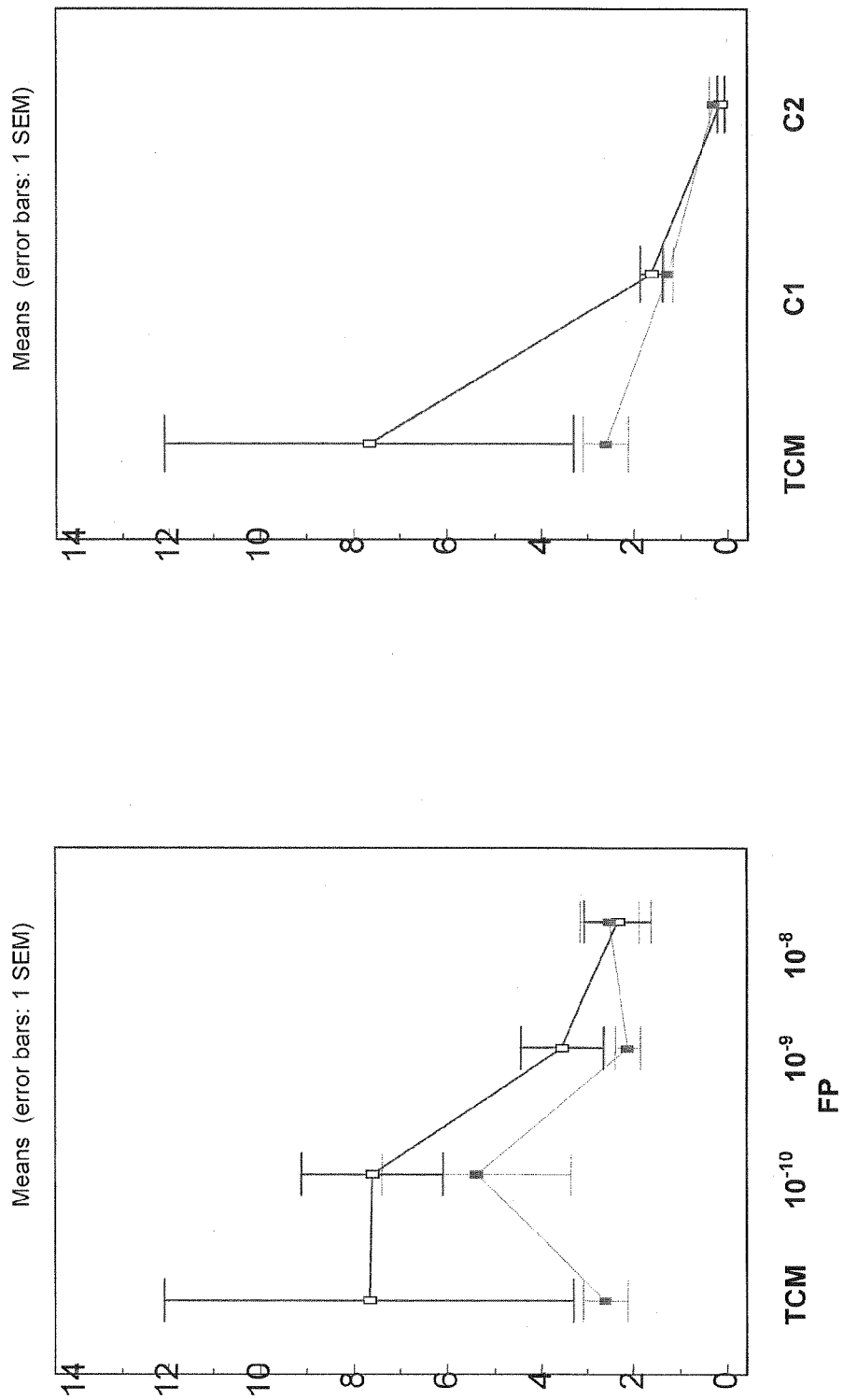
Figure 13:
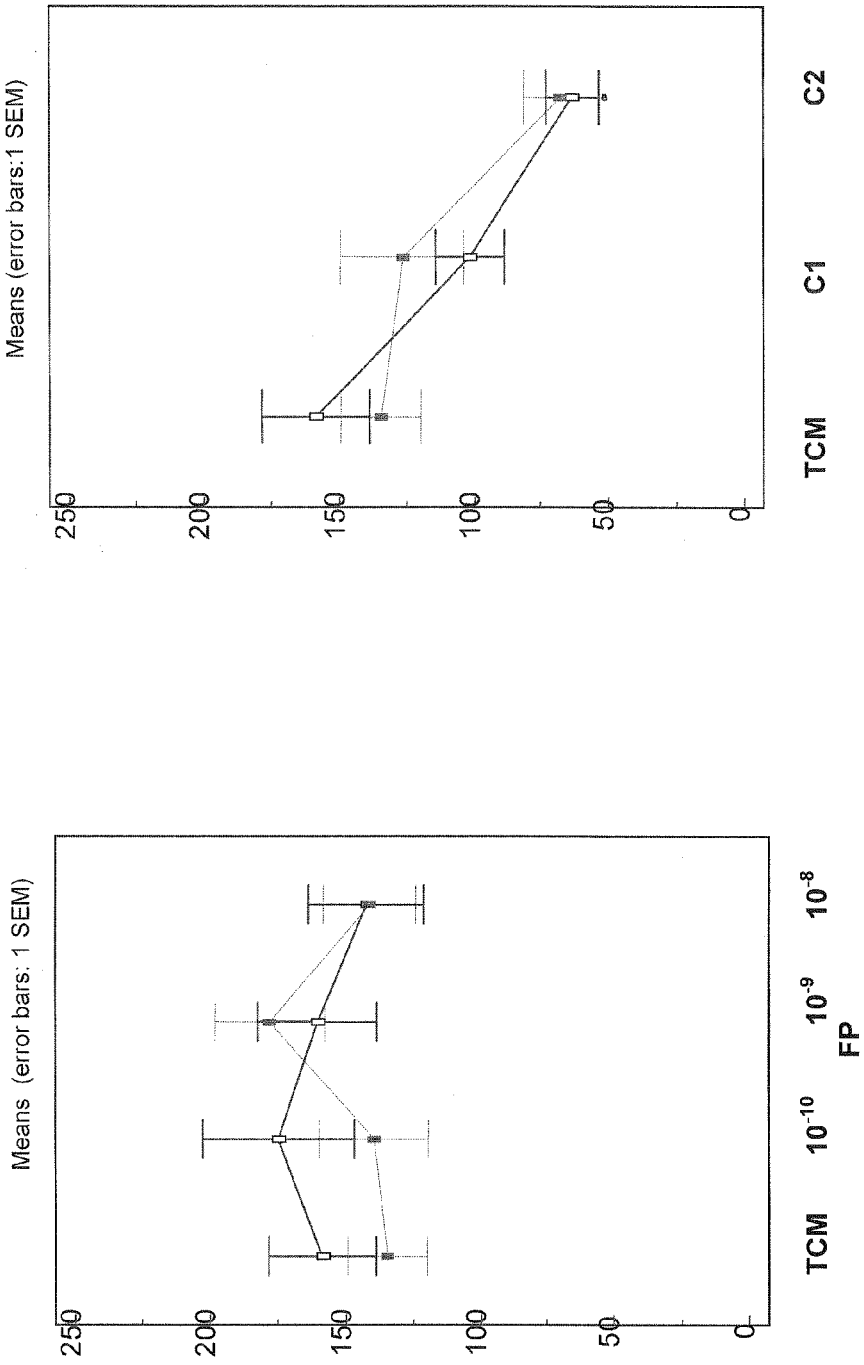
Figure 14:
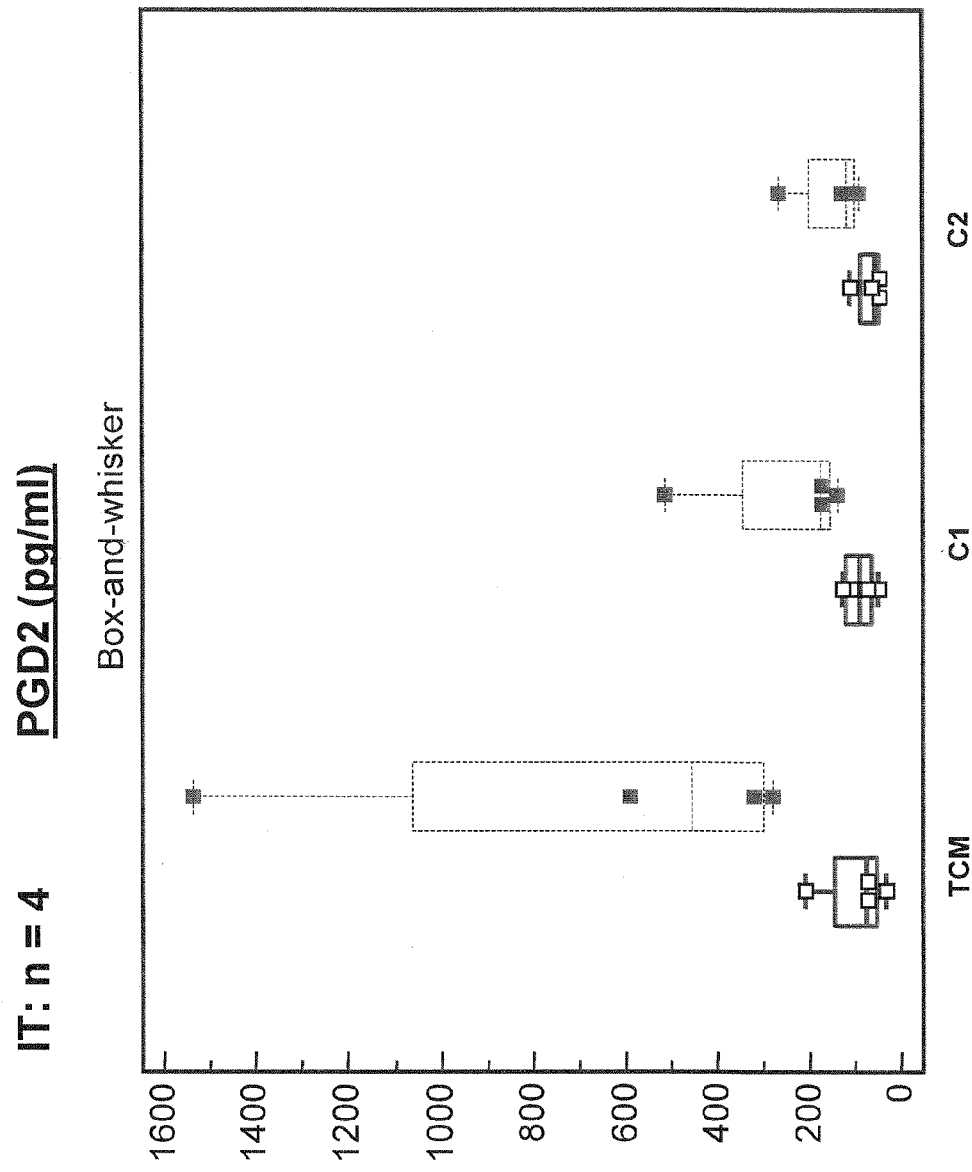

The results for the testing of IL-2 (general T-cell activation marker) are shown in FIG. 3. It is shown that SEB results in a strong increase, which is only partially inhibited by FP, but substantially inhibited by the herbal-based nasal solution (C1).

The results for the testing of IFN-γ (Th1-cell marker) are shown in FIG. 4. It is shown that SEB results in a strong increase, which is only partially inhibited by FP, but substantially inhibited by the herbal-based nasal solution (C1).

The results for the testing of IL-4 (Th2-cell marker) are shown in FIG. 5. It is shown that SEB results in a modest increase, which is substantially inhibited by FP and the herbal-based nasal solution (C1). The spontaneous release of IL-4 is also inhibited by the herbal-based nasal solution (C1).

The results for the testing of IL-5 (Th2-cell marker) are shown in FIG. 6. It is shown that SEB results in a modest increase, which is substantially inhibited by FP. The SEB-induced and spontaneous release of IL-5 is substantially inhibited by the herbal-based nasal solution (C1).

The results for the testing of IL-13 (Th2-cell marker) are shown in FIG. 7. It is shown that SEB results in a modest increase, which is substantially inhibited by FP. The SEB-induced and spontaneous release of IL-13 is markedly inhibited by the herbal-based nasal solution (C1).

The results for the testing of IL-17 (Th-17-cell marker) are shown in FIG. 8. It is shown that SEB results in a strong increase, which is only partially inhibited by FP, but substantially inhibited by the herbal-based nasal solution (C1).

The results for the testing of IL-1β (pro-inflammatory cytokine) are shown in FIG. 9. It is shown that SEB results in a modest increase, which is hardly inhibited by FP. However, the spontaneous and induced release of IL-1β is inhibited by the herbal-based nasal solution (C1).

The results for the testing of TNF-α (pro-inflammatory cytokine) are shown in FIG. 10. It is shown that SEB results in a modest increase, which is not inhibited by FP. However, the spontaneous and SEB-induced release of IL-1β is inhibited by the herbal-based nasal solution (C2).

The results for the testing of IL-10 (regulatory cytokine) are shown in FIG. 11. It is shown that there is substantially minimal impact of SEB or FP. The spontaneous release of IL-10 is substantially inhibited by the herbal-based nasal solution (C1).

The results for the testing of IL-12 p70 (Th1-related cytokine) are shown in FIG. 12. It is shown that SEB results in a modest increase, which is substantially inhibited by FP and the herbal-based nasal solution (C1). However, the spontaneous release of IL-12 p70 is substantially inhibited by the herbal-based nasal solution only (C2).

The results for the testing of TGF-β (remodelling and regulatory cytokine) are shown in FIG. 13. It is shown that there is substantially little impact of SEB or FP. However, there is a dose-dependent suppression of spontaneous TGF-β1 release by the herbal-based nasal solution.

In summary, T-cells orchestrate immune defense and inflammation; currently, 3 major T effector cells are described (Th1, Th2 and Th17-cells). These cells are important in different forms of inflammation and substantially impact the composition of inflammatory cells (eosinophilic vs. neutrophilic), and also induce pathogenic changes such as mucus production, remodelling etc. Th2, Th1 and Th17 cells have been implicated in chronic diseases of the paranasal sinuses, i.e. Th1-related cytokine IFN-γ in chronic rhinosinusitis without nasal polyps (CRSsNP), Th2-related cytokines IL-4 and IL-5 in CRS with nasal polyps (CRSwNP) and recently Th17-cell related IL-17 in Asian nasal polyps and polyps in cystic fibrosis patients. As those cytokines may also present within the same tissue, a drug with a broad range of activities on different T-cells is needed to efficiently down-regulate inflammation.

The herbal-based nasal solutions tested are seen to have a unique and improved effect when compared to fluticasone propionate activity to down-regulate a range of cytokines of major T-cell types, including the major Th1, Th2 and Th17 cytokines, upon SEB stimulation, but also under spontaneous release conditions. It is therefore uniquely positioned to act as topically applied anti-inflammatory formulation in nasal polyp disease of whatever type (Caucasian, Asian, cystic fibrosis). Similarly, it could be used to treat other inflammatory conditions unrelated to the airways, if sufficient concentrations can be achieved via an oral route.

The herbal-based nasal solutions tested also inhibited TGF-β1, which differentiates it from fluticasone propionate. As TGF-β1 is the key cytokine in chronic rhinosinusitis with nasal polyps (CRSwNP), causing fibrosis, this disease may be treatable, if access to the sinuses can be obtained.

The herbal-based nasal solution may also be useful in treating allergic mucosal disease, as it reduces the release of allergic late-phase cytokines such as IL-4, IL-5 and IL-13. Furthermore, upon testing, the herbal-based nasal solution has a substantially strong inhibitory effect on the release of mast cell mediators after anti-IgE stimulation (so-called early phase mediators). This stimulation represents the early phase response (within about 30 minutes) after allergen exposure in allergic rhinitis subjects. An anti-IgE concentration of about 10 µg/ml, within about thirty minutes, induced a substantial release of prostaglandin D2 (PGD2), a representative early phase mediator, from the mast cells. This response was dose-dependently suppressed by the herbal-based nasal solution at 0.5 and 2.5-fold concentrations as seen in FIG. 14.

From a historical perspective, initial studies with Scutellaria radix extract at a concentration of 20 µg/ml reduced PGD2 and histamine release from mast cells upon anti-IgE stimulation by at least 50%. Furthermore, Scutellaria, at a concentration of 2 µg/ml had a minimal effect on interferon-gamma release from T-cells upon stimulation with staphylococcal enterotoxin B, a T-cell activator. Still further studies with Scutellaria radix extract at a concentration of 10 µg/ml showed some minimal effect on IL-2 release.

Therefore, it was determined that there was a need to increase the potency of Scutellaria radix extract in order to achieve an increase in the activity on T-cell cytokines released in the late-phase allergic reaction and in other types of airway disease. In order to reach this goal, a search was initiated within the group of herbal extracts with potential anti-inflammatory activity. This search lead to the combination of herbal extracts including of Scutellaria radix with Eleutherococcus radix, chamomile and ascorbic acid at a ratio of 1:1:2:1, which demonstrated to be even more effective on the mast cell release of mediators during the allergic early phase reaction (at a concentration as low as 1 µg/ml), and to have anti-inflammatory activities against a range of cytokines, such as IL-5 (important in the allergic late phase reaction), IFN and IL-17 (relevant in neutrophilic inflammations) and pro-inflammatory cytokines IL-1 and TNF (involved in common cold and acute infections) at a concentration of 10 µg/ml. This approach resulted in a doubling of the activity against allergic disease (early and late phase mediators, allowing the combination of a rapid onset of action with a truly anti-inflammatory effect on the long term), as well as an expansion of the spectrum of diseases treatable by Scutellaria, including chronic rhinosinusitis, acute rhinosinusitis, nasal polyps, the common cold, chronic obstructive pulmonary disease (COPD), and asthma.

Figure 15:
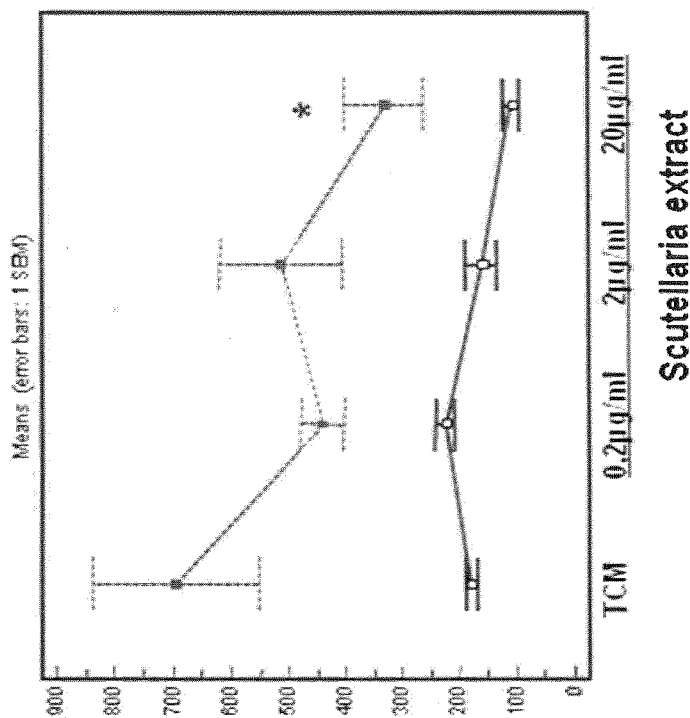
Figure 16:
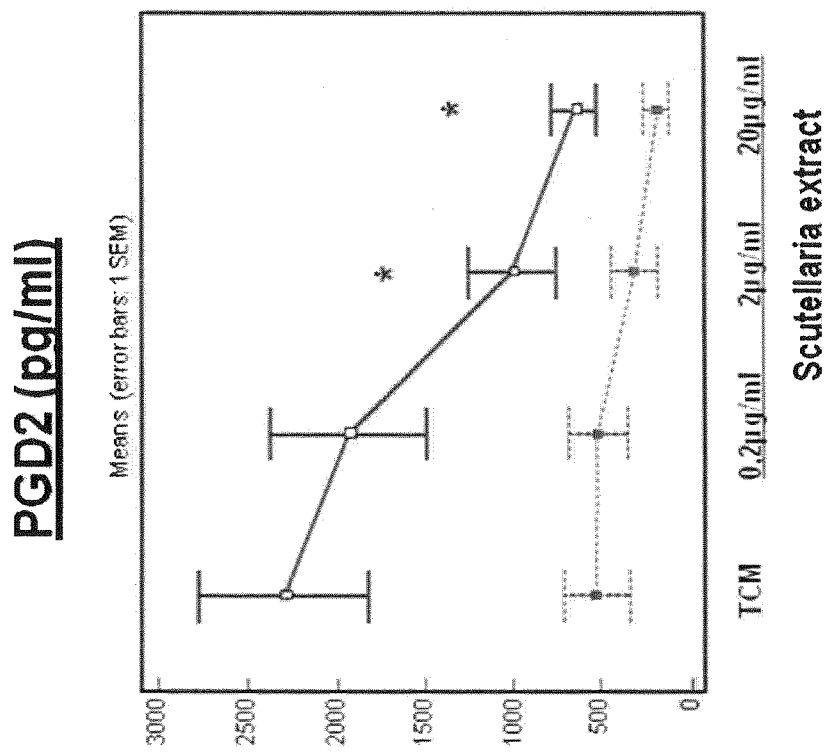

In yet further studies to determine the optimal inhibitory activity on mast cell degranulation, a Scutellaria extract was tested in a dose-response experiment using ex-vivo nasal inferior with anti-IgE stimulation, as seen in FIG. 15, and polyp tissue with anti-IgE stimulation, as seen in FIG. 16, as previously described herein.

These tests showed that the Scutellaria extract, prepared by a standard 60% ethanol extraction with a final concentration of 0.06% of ethanol and tested in concentrations of 0.2 to 20 µg/ml, reduced PGD2 release from mast cells into the tissue in a dose-dependent manner. This reduction reached significance at a concentration of 20 µg/ml in inferior turbinate tissue, as seen in FIG. 15, and at a concentration of 2 µg/ml in nasal polyp tissue, as seen in FIG. 16, versus a baseline of anti-IgE stimulation without active component.

In one embodiment of the invention, the herbal-based nasal solution may be administered topically as a nasal spray via a metered-dose spray device, as nasal drops, as nasals, or injection into the nasal membrane or the sinuses. In another embodiment, the herbal-based nasal solution may be formulated into a topical cream for oral and topical application.

The herbal-based nasal solution may be considered a therapeutically effective nasal solution which means that the solution is generally effective to achieve the desired effects of relieving the symptoms and shortening the duration of nasal inflammation. As PGD2 is a specific marker indicating mast cell degranulation, the inhibition of release of other mediators such as histamine, leukotrienes and PAF also can be affected by Scutellaria. Therefore, it is envisioned that the herbal-based nasal solution may be useful in the inhibition of the allergen-induced early phase in allergic rhinitis, allergic conjunctivitis, allergic dermatitis, conjunctivitis, asthma, as well as other conditions characterized by mast cell degranulation and IgE-mediated release including allergic skin and bowel disorders (food allergy, oral allergy syndrome), urticaria, and insect stings.

Based on the foregoing disclosure, it should be apparent that the herbal-based nasal solution and method for treating nasal inflammation of the invention will achieve the objectives set forth above. It is therefore understood that any evident variations will fall within the scope of the claimed invention. Thus, alternate specific component elements can be selected without departing from the spirit of the invention disclosed and described herein.

What is claimed is:

1. A nasal solution for treating nasal and sinus inflammation comprising:
   0.01 to 0.20% by weight of vitamin C;
   0.02 to 0.50% by weight of an extract of scutellaria radix;
   0.02 to 0.50% by weight of an extract of eleutherococcus radix;
   0.1 to 1.0% by weight of an extract of chamomile;
   0.01 to 0.15% by weight of a lubricating agent; and
   98.70 to 99.90% by weight of a pharmaceutically acceptable carrier.

2. The nasal solution of claim 1, wherein the lubricating agent is glycerol.

3. The nasal solution of claim 1, wherein the pharmaceutically acceptable carrier is selected from the group consisting of Ringer's lactate solution and isotonic saline solution.

4. The nasal solution of claim 1, wherein the nasal solution is usable for treating allergic mucosal disease.

5. The nasal solution of claim 4, wherein the nasal solution is capable of suppressing early phase and late phase mediators of allergic mucosal disease.

6. The nasal solution of claim 5, wherein the early phase mediator is prostaglandin D2.

7. The nasal solution of claim 5, wherein the late phase mediators are selected from the group consisting of IL-4, IL-5, and IL-I 3.

* * * * *